(12) United States Patent
Zobel et al.

(10) Patent No.: US 6,544,929 B2
(45) Date of Patent: Apr. 8, 2003

(54) HERBICIDAL COMPOSITIONS

(75) Inventors: Jean-Claude Zobel, Lyons (FR); Anne-Claire Rouanet, Brignais (FR)

(73) Assignee: Aventis CropScience S.A., Lyons (FR)

( * ) Notice: Subject to any disclaimer, the term of this patent is extended or adjusted under 35 U.S.C. 154(b) by 0 days.

(21) Appl. No.: 09/875,007

(22) Filed: Jun. 7, 2001

(65) Prior Publication Data

US 2002/0039969 A1 Apr. 4, 2002

(30) Foreign Application Priority Data

Jun. 7, 2000 (EP) .............................. 00112181

(51) Int. Cl.⁷ ................................. A01N 57/00
(52) U.S. Cl. ...................................... 504/128
(58) Field of Search ............................... 504/116.1, 128

(56) References Cited

FOREIGN PATENT DOCUMENTS

| EP | 0194146 A | | 9/1986 |
|---|---|---|---|
| EP | 0431361 A | | 6/1991 |
| JP | 09124421 | * | 5/1997 |
| WO | 97/34486 A | | 9/1997 |
| WO | 9854967 | * | 12/1998 |
| WO | 99/23886 | | 5/1999 |
| WO | 00/25584 A | | 5/2000 |

* cited by examiner

*Primary Examiner*—Alton Pryor
(74) *Attorney, Agent, or Firm*—Burns, Doane, Swecker & Mathis, L.L.P.

(57) ABSTRACT

A herbicidal composition comprising:
 (a) isoxaflutole;
 (b) glyphosate or glufosinate or a salt thereof; and
 (c) a stabilizing amount of at least one compound selected from
  (i) glycol,
  (ii) polyethylene glycol,
  (iii) polypropylene glycol,
  (iv) glycerol,
  (v) esters of (i) to (iv), and
  (vi) ethers of (i) to (iv).

40 Claims, No Drawings

HERBICIDAL COMPOSITIONS

CROSS-REFERENCE TO PRIORITY APPLICATION

This application claims priority under 35 U.S.C. §119 of European Application No. EP 00112181.3, filed Jun. 7, 2000, the entire disclosure of which is hereby expressly incorporated by reference.

This invention relates to novel herbicidal compositions comprising isoxaflutole, glyphosate or glufosinate herbicide and a stabilizing agent.

In PCT/EP 98/07514 there are described compositions comprising isoxaflutole and glyphosate. Results are disclosed of tank mixture trials of the herbicides which demonstrated a biological synergy between the mixtures.

A problem however, which may exist with isoxazole derivatives such as isoxaflutole, is their instability under certain conditions. For example, in the presence of bases and certain adjuvants, the compounds can undergo ring opening to give a 1,3-dione compound. This can lead to difficulties in producing pre-mixed formulations containing an isoxazole and a partner herbicide.

Mixtures of glyphosate and a partner herbicide may provide an effective level of weed control, however, problems may arise where the two component formulations, e.g. of glyphosate and the partner herbicide, are incompatible, e.g. physically or chemically, with each other. For example, in a tank mix formulation, isoxaflutole may be degraded by the presence of certain adjuvant components necessary for glyphosate efficacy.

Chemical or physical incompatibility may also be significant in "pre-mix" formulations comprising two or more herbicides. Such formulations are often preferred as they ensure correct application rates of herbicides are applied to the locus.

The applicants have found that the presence of glycol, or polymers thereof and/or glycerol in "pre-mix" compositions comprising isoxaflutole and glyphosate or glufosinate improve the stability of isoxaflutole. Furthermore, activity on certain grass and broad leaf weeds may be improved.

Thus according to the invention there is provided a composition comprising:
(a) isoxaflutole;
(b) glyphosate or glufosinate and salts thereof; and
(c) a stabilizing amount of at least one compound selected from
(i) glycol,
(ii) polyethylene glycol,
(iii) polypropylene glycol,
(iv) glycerol,
(v) esters of (i) to (iv), and
(vi) ethers of (i) to (iv).

In the description that follows, unless otherwise specified, the percentages are by weight.

The compositions of the invention generally contain up to 90%, especially up to 75%, of active ingredients (i.e. components (a), (b) and (c) above), although it will be understood that this amount may vary depending on the nature of the composition and the solubility and/or dispersibility of the various components. Preferably the composition contains up to 55% of active ingredients, more preferably from 20 to 55%.

It will be understood that the glycol is generally a polymer of formula (I) or (II);

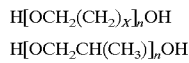

$$H[OCH_2(CH_2)_x]_nOH \qquad (I)$$
$$H[OCH_2CH(CH_3)]_nOH \qquad (II)$$

wherein x is preferably one or two;
and n is such that the overall weight of the molecule is from 50 to 10,000, preferably from 200 to 600.

Examples of esters of the glycols or glycerol include allate, caprylate, cocoate, laurate, myristate, oleate, ricinolate and stearate esters. Compositions comprising polyethylene glycol are generally preferred.

Generally the amount of (c) is from 15 to 65% of the composition weight, although the exact amount may vary depending on the specific glycol present and the nature of the other formulants present.

Glyphosate which is N-(phosphonomethyl)glycine, is usually present in its acid form or as a derivative thereof, such as the isopropylammonium salt or the trimesium (trimethylsulfoxonium) salt. Glufosinate which is 4-[hydroxy(methyl)phosphinoyl]-DL-homoalanine, is usually present as the ammonium salt.

It will be understood that in certain cases the stability of the glyphosate or glufosinate herbicide may also depend on factors such as pH, and that the pH of the mixture may need to be adjusted by the skilled worker accordingly. Preferably the pH of the composition is in the range from 2 to 7, more preferably from 2.0 to 5.0.

The compositions of the invention are preferably provided in the form of pre-mixed formulations. Preferred formulations are in the form of suspension concentrates, emulsifiable concentrates, a gel, a suspo-emulsion, an emulsion concentrate, a wettable powder or a water dispersible granule or powder. Compositions in the form of suspension concentrates are particularly preferred.

Compositions of the present invention may be in association with, and are preferably homogeneously dispersed in, one or more compatible agriculturally-acceptable diluents or carrier and/or surface active agents [i.e. diluents or carriers and/or surface active agents of the type generally accepted in the art as being suitable for use on herbicidal compositions and which are compatible with components (a), (b) and (c)]. The term "homogeneously dispersed" is used to include compositions in which the components (a), (b) and (c) are dissolved in other components. The term "herbicidal compositions" is used in a broad sense to include not only compositions which are ready for use as herbicides but also concentrates which must be diluted before use. The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethythene oxide with alkyl and polyaryl phenols, e.g. nonyl- or octyl-phenols, tristyryl phenols, condensates of ethylene oxide with alcohols, or carboxylic acid esters of any hydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher portions of surface-active agent, for example up to 15% by weight in liquid emulsifiable suspension concentrates and up to 25% by weight in liquid water soluble concentrates.

Examples of suitable solid diluents or carriers are aluminium silicate, microfine silicon dioxide, talc, chalk, calcined magnesia, kieselguhr, tricalcium phosphate, powdered cork, adsorbent carbon black and clays such as kaolin, attapulgite, diatomaceous earth, mica, alumina oxide, titanium oxide and bentonite. The solid compositions (which may take the form of dusts, granules or wettable powders) are preferably prepared by grinding the components (a), (b) and (c) with solid diluents or by impregnating the solid diluents or carriers with solutions of components (a), (b) and (c) in volatile solvents, evaporating the solvents and if necessary, grinding the products so as to obtain powders. Granular formulations may be prepared by absorbing components (a), (b) and (c) dissolved in suitable solvents, (which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, tetrahydrofurfuyl alcohol, acetophenone, cyclohexanone, isophorone, alkyl pyrrolidones, butylolactone, chlorinated toluene, xylene, mineral, animal and vegetable oils, esterified vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the components (a), (b) and (c) may be used in the form of self-emulsifying concentrates containing the active substances dispersed in the emulsifying agents or in solvents containing emulsifying agents compatible with the active substances, the simple addition of such concentrates to water producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, spreading agents, buffers, sequestering agents, anti-caking agents, coloring agents and corrosion inhibitors. These adjuvants may also serve as carriers or diluents.

Unless otherwise specified, the following percentages are by weight. Preferred herbicidal compositions according to the present invention are aqueous suspension concentrates which comprise from 5 to 70% of components (a), (b) and (c), from 2 to 10% of surface-active agent, from 0.1 to 5% of thickener and from 15 to 87.9% of water;

wettable powders which comprise from 5 to 90% of components (a), (b) and (c), from 2 to 10% of surface-active agent and from 8 to 88% of solid diluent or carrier;

water dispersible granules which comprise from 1 to 90%, e.g. 25 to 75% of components (a), (b) and (c), from 1 to 15%, e.g. 2 to 10%, of surface-active agent and from 5 to 95%, e.g. 20 to 60%, of solid diluent, e.g. clay, granulated with the addition of water to form a paste and then dried;

water soluble or water dispersible powders which comprise from 5 to 90% of components (a), (b) and (c), from 2 to 40% of sodium carbonate and from 0 to 88% of solid diluent;

liquid water soluble concentrates which comprise from 5 to 50%, e.g. 10 to 30% of components (a), (b) and (c), from 0 to 25% of surface-active agent and from 10 to 90%, e.g. 45 to 85%, of water miscible solvent, or a mixture or water-miscible solvent and water;

liquid emulsifiable suspension concentrates which comprise from 5 to 70% of components (a), (b) and (c), from 5 to 15% of surface-active agent, from 0.1 to 5% of thickener and from 10 to 84% of organic solvent, e.g. mineral oil; and emulsifiable concentrates which comprise 0.05 to 90%, and preferably from 1 to 60% of components (a), (b) and (c), from 0.01 to 10%, and preferably from 39 to 98.99%, of organic solvent.

Herbicidal compositions according to the present invention may also comprise components (a), (b) and (c) in association with, and preferably homogeneously dispersed in, one or more other pesticidally active compounds and, if desired, one or more compatible pesticidally diluents or carriers, surface-active agents and conventional adjuvants as hereinbefore described.

Examples of other pesticidally active compounds which may be included in, or used in conjunction with, the herbicidal compositions of the present invention include herbicides, for example those listed in the Pesticide Manual 11th Edition (British Crop Protection Council).

The present invention further provides a method for controlling the growth of weeds at a locus which comprises applying to said locus a herbicidally effective amount of:
  (a) isoxaflutole;
  (b) glyphosate or glufosinate and salts thereof; and
  (c) a stabilizing amount of at least one compound selected from
    (i) glycol,
    (ii) polyethylene glycol,
    (iii) polypropylene glycol,
    (iv) glycerol,
    (v) esters of (i) to (iv), and
    (vi) ethers of (i) to (iv).

Weeds that may be controlled by the method of the invention include grass weeds, broad-leaf weeds and sedges. Examples of grass weeds include *Alopecurus myosuroides, Avenafatua, Digitaria sanguinalis, Echinochloa crusgalli, Sorghum bicolor, Eleusine indica* and Setaria spp, e.g. Setariafaberii or *Setaria viridis*.

Examples of broad-leaf weeds include *Abutilon theophrasti, Amaranthus retroflexus, Bidens pilosa, Chenopodium album, Galium aparine*, Ipomoea spp. e.g. *Ipomoea purpurea, Sesbania exaltata, Sinapis arvensis, Solanum nigrum* and *Xanthium strumarium*.

An example of a sedge includes *Cyperus esculentus*.

The crop species which may be used in the method of the invention include maize, soybean, cotton, canola, sugar beet, potatoes, wheat, tobacco, rice and oil seed rape. Preferred crops include maize, sugar beet, soybean, cotton and canola. Particularly preferred crop species are maize and soybean, especially maize.

Preferably the crop has been genetically manipulated to confer enhanced tolerance to isoxaflutole, glyphosate or glufosinate herbicides.

In general the application rate of isoxaflutole is from 20 gha$^{-1}$ to 500 gha$^{-1}$, preferably from 50 gha$^{-1}$ to 150 gha$^-$; the application rate of glyphosate is from 250 g to 3000 g acid equivalent (a.e.)/ha, preferably from 400 g to 1000 g (a.e.)/ha; and the application rate of glufosinate is from 100 g to 2000 g/ha, preferably from 250 g to 1000 g (a.e.)/ha. It will be understood that the application rates used will depend on the growth stage of the weeds, the climatic conditions, the time of application, the type of weeds present, the crops and other parameters apparent to the skilled worker.

Preferably the weight ratio of isoxaflutole:glyphosate is from 1:150 to 2:1, more preferably from 1:20 to 1:2.7. Preferably the weight ratio of isoxaflutole:glufosinate is from 1:100 to 5:1, more preferably from 1:20 to 1:1.67.

According to a feature of the present invention the method comprises treating a crop locus with a composition comprising isoxaflutole, glyphosate or glufosinate and a compound selected from glycol, polyethylene glycol, polypropylene glycol, glycerol, or esters and ethers thereof, to provide total weed control.

According to a further feature of the present invention the method comprises controlling the growth of weeds at a crop locus, by the application of a composition comprising isoxaflutole and glyphosate or glufosinate and a compound selected from glycol, polyethylene glycol, polypropylene glycol, glycerol, or esters and ethers thereof, said crop having been genetically modified to confer enhanced tolerance to isoxaflutole, glyphosate or glufosinate herbicides.

The following Examples illustrate the invention. Unless otherwise stated percentages are by weight.

Compositions comprising isoxaflutole, glyphosate, various glycol polymers and glycerol were prepared and their stability analyzed. To determine the stability, the formulations were placed in 10–20 ml glass vials, which were hermetically closed (with a tap); stored at the specified temperature for the specified length of time then removed, allowed to cool at room temperature, sampled and analyzed. The method of analysis was as follows. Each formulation mixture was analyzed for the proportion of isoxazole present using standard High Performance Liquid Chromatography (HPLC) technology. This involves weighing a known amount of sample into a solvent system of methanol containing 1% trifluoroacetic acid followed by injecting a known aliquot into the HPLC system. The extracted sample is passed through a column (for example a Plurosphere NP 18 encapped column) packed with sorbent. Following elution the various components of the compositions are separated depending upon varying sorption capacities/hydrophilicity. The amount of the component is determined by the amount of ultraviolet light absorbed at specific wavelengths of the ultraviolet light. The amount of degradation is calculated based upon the difference between the initial and stored analyzed component content.

EXAMPLE 1

A suspension concentrate (SC) was prepared comprising glyphosate acid 240 g/l and isoxaflutole 30 g/l. Glycol polymer (120 g/l) and glycerol (120 g/l) were added as individual components or in combination and the formulations were stored at 54° C. The percentage degradation of isoxaflutole (IFT) was determined after 14 days.

TABLE 1

DEGRADATION OF IFT IN SC FORMULATIONS COMPRISING GLYPHOSATE.

| Formulation | % degradation of IFT (14 days at 54° C.) |
| --- | --- |
| SC IFT + glyphosate | 1.7 |
| SC IFT + glyphosate + glycerol | 17 |
| SC IFT + glyphosate + PEG | 20 |
| SC IFT + glyphosate + glycerol + PEG | 7.5 |

EXAMPLE 2

Seed of *Setaria viridis* were sown and SC formulations comprising isoxaflutole (75 g/ha), glyphosate acid (600 g/ha), glycol polymer (120 g/l) (polyethylene glycol, PEG) and glycerol (120 g/l) were applied pre emergence in a water diluted form using a laboratory sprayer. A tank mix formulation of isoxaflutole (used as the commercial formulation "Balance", trade mark, a wettable dispersible granule, 75 g/ha) and glyphosate (used as the commercial formulation "Roundup", trade mark, a soluble concentrate, 600 g/ha) was prepared by combining the two component formulations in water. The resultant tank mix was sprayed immediately by pre emergence application to the soil. A visual assessment was made 14 days after treatment (DAT).

In the table that follows the figures for weed control are percentage reductions in growth when compared with untreated controls.

TABLE 2

ACTIVITY OF SC FORMULATIONS OF IFT AND GLYPHOSATE ON *SETARIA VIRIDIS*.

| Formulation | % Activity | |
| --- | --- | --- |
| | Pre-emergence | Post-emergence |
| SC IFT + glyphosate | 35 | 50 |
| SC IFT + glyphosate + glycerol | 75 | 80 |
| SC IFT + glyphosate + PEG | 70 | 90 |
| SC IFT + glyphosate + glycerol + PEG | 80 | 100 |
| IFT + glyphosate (tank mix) | 80 | 100 |

EXAMPLE 3

Seed of the grass weed species ECHCG, ELUIN, SETVI, SETFA and broad leaf weed species, ABUTH, AMARE, PHBPU, XANST were sown. A tank mix formulation of isoxaflutole and glyphosate (as described in EXAMPLE 2) was prepared by combining the two component formulations in water. The resultant tank mix was sprayed immediately by pre emergence application to the soil. 'Pre-mix' SC formulations comprising isoxaflutole, glyphosate acid, glycol polymer (120 g/l) (polyethylene glycol, PEG) and glycerol (120 g/l) were applied pre emergence in a water diluted form using a laboratory sprayer. A visual assessment was made 14 and 21 days after treatment (DAT). Results are given as an average activity on grass and broad leaf weed species.

TABLE 3

ACTIVITY OF SC AND TANK MIX FORMULATIONS OF IFT
AND GLYPHOSATE ON GRASS WEED SPECIES (14DAT).

| Glyphosate | IFT | % Activity (14DAT) | |
|---|---|---|---|
| (g/ha) | (g/ha) | Tank-mix | SC |
| 150 | 18.75 | 30 | 30 |
| 300 | 37.5 | 27 | 61 |
| 600 | 75 | 51 | 71 |
| 1200 | 150 | 96 | 79 |

TABLE 4

ACTIVITY OF SC AND TANK MIX FORMULATIONS OF IFT
AND GLYPHOSATE ON GRASS WEED SPECIES (21DAT).

| Glyphosate | IFT | % Activity (21DAT) | |
|---|---|---|---|
| (g/ha) | (g/ha) | Tank-mix | SC |
| 150 | 18.75 | 30 | 30 |
| 300 | 37.5 | 18 | 50 |
| 600 | 75 | 40 | 72 |
| 1200 | 150 | 94 | 76 |

TABLE 5

ACTIVITY OF SC AND TANK MIX FORMULATIONS OF IFT
AND GLYPHOSATE ON BROAD LEAF WEED SPECIES (14DAT).

| Glyphosate | IFT | % Activity (14DAT) | |
|---|---|---|---|
| (g/ha) | (g/ha) | Tank-mix | SC |
| 150 | 18.75 | 54 | 73 |
| 300 | 37.5 | 65 | 89 |
| 600 | 75 | 77 | 69 |
| 1200 | 150 | 85 | 79 |

TABLE 6

ACTIVITY OF SC AND TANK MIX FORMULATIONS OF IFT
AND GLYPHOSATE ON BROAD LEAF WEED SPECIES (21DAT).

| Glyphosate | IFT | % Activity (21DAT) | |
|---|---|---|---|
| (g/ha) | (g/ha) | Tank-mix | SC |
| 150 | 18.75 | 34 | 65 |
| 300 | 37.5 | 49 | 90 |
| 600 | 75 | 84 | 88 |
| 1200 | 150 | 95 | 93 |

EXAMPLE 4

Seed of various weed species, ECHCG, ELUIN, SETVI, SETFA, ABUTH, AMARE, PHBPU, XANST and crop species MAIZE and SOYA, were sown and and SC formulation comprising isoxaflutole (75 g/ha), glyphosate acid (600 g/ha), glycol polymer (120 g/l) (polyethylene glycol, PEG) and glycerol (120 g/l) was applied pre emergence in a water diluted form using a laboratory sprayer. A tank mix formulation of isoxaflutole and glyphosate (as described in EXAMPLE 2) was prepared by combining the two component formulations in water. The resultant tank mix was sprayed immediately by pre emergence application to the soil. A visual assessment was made 21 days after treatment (DAT).

TABLE 7

PRE EMERGENCE ACTIVITY OF AN SC AND TANK MIX
FORMULATION OF IFT AND GLYPHOSATE.

| SPECIES | Tank Mix | SC formulation |
|---|---|---|
| Grass Weeds | | |
| ECHCG | 100 | 100 |
| ELUIN | 50 | 95 |
| SETVI | 20 | 100 |
| SETFA | 50 | 80 |
| Broad Leaf Weeds | | |
| ABUTH | 95 | 100 |
| AMARE | 95 | 90 |
| PHBPU | 90 | 90 |
| XANST | 50 | 90 |
| Crops | | |
| MAIZE | 0 | 0 |
| SOYA | 70 | 40 |

It will be seen that the foregoing results demonstrate the suspension concentrate formulations of the invention, in the presence of a glycol polymer and/or glycerol, reduce the degradation of isoxaflutole and are of comparable efficacy with a commercial tank mix.

The SC formulations also show improved activity on Setaria spp., *Eleusine indica* and *Xanthium strumarium*, and improved selectivity on soya.

Such efficacy and activity is surprising as the suspension concentrate formulations of the present invention comprise the acid form of glyphosate which is usually less efficacious than the glyphosate salt derivative used in commercial formulations.

What is claimed is:

1. A herbicidal composition comprising a herbicidally effective amount of:
    (a) isoxaflutole;
    (b) glyphosate; and
    (c) a combined amount of (I) polyethylene glycol and (ii) glycerol;
    said combined amount of (i) and (ii) being an amount effective to enhance the combined herbicidal activity of (a) and (b).

2. A composition according to claim 1, in which the percentage by weight of polyethylene glycol and glycerol present in the composition is from 15 to 65%.

3. A composition according to claim 1, which is in the form of a pre-mixed formulation.

4. A composition according to claim 1, in which the composition is in the form of a suspension concentrate, an emulsifiable concentrate, a gel, a suspo-emulsion, an emulsion concentrate, a wettable powder or a water dispersible granule or powder.

5. A method for controlling the growth of weeds at a locus which comprises applying to said locus a herbicidally effective amount of:
    (a) isoxaflutole;
    (b) glyphosate; and
    (c) a combined amount of (i) polyethylene glycol and (ii) glycerol;
    said combined amount of (i) and (ii) being an amount effective to enhance the combined herbicidal activity of (a) and (b).

6. A method according to claim 5, which the locus is a crop selected from maize, sugar beet, soybean, cotton and canola.

7. A method according to claim 5, which the locus is a crop which maize or soybean.

8. A method according to claim 5, in which the locus is a crop selected from maize, sugar beet, soybean, cotton and canola and has been genetically manipulated to confer enhanced tolerance to isoxaflutole or glyphosate.

9. A method according to claim 5, in which the application rate of isoxaflutole is from 20 $gha^{-1}$ to 500 $gha^{-1}$.

10. A method according to claim 5, in which the application rate of isoxaflutole is from 50 $gha^{-1}$ to 150 $gha^{-1}$.

11. A method according to claim 5, in which the application rate of glyphosate is from 250 g to 3000 g acid equivalent (a.e.)/ha.

12. A method according to claim 5, in which the application rate of glyphosate is from 400 g to 1000 g acid equivalent (a.e.)/ha.

13. A method according to claim 5, which the weight ratio of isoxaflutole to glyphosate is from 1:150 to 2:1.

14. A method according to claim in which the weight ratio of isoxaflutole to glyphosate is from 1:20 to 1:2.7.

15. A method for controlling the growth of weeds at a locus which comprises applying to said locus a herbicidal composition comprising a herbicidally effective amount of:
   (a) isoxaflutole;
   (b) glyphosate; and
   (c) a combined amount of (i) polyethylene glycol and (ii) glycerol;
   said combined amount of (i) and (ii) being an amount effective to enhance the combined herbicidal activity of (a) and (b).

16. A herbicidal composition comprising a herbicidally effective amount of:
   (a) isoxaflutole;
   (b) glyphosate; and
   (c) a combined amount of (i) polyethylene glycol and (ii) glycerol;
   said composition being in the form of a suspension concentrate;
   said combined amount of (i) and (ii) being an amount effective to improve the chemical stability of (a) in said suspension concentrate.

17. A composition according to claim 16, in which die percentage by weight of polyethylene glycol and glycerol present in the composition is from 15 to 65%.

18. A method for controlling the growth of weeds at a locus which comprises applying to said locus a herbicidal composition comprising a herbicidally effective amount of:
   (a) isoxaflutole;
   (b) glyphosate; and
   (c) a combined amount of (i) polyethylene glycol and (ii) glycerol;
   said composition being in the form of a suspension concentrate;
   said combined amount of (i) and (ii) being an amount effective to improve the chemical stability of (a) in said suspension concentrate.

19. A method according to claim 18, in which the locus is a crop selected from maize, sugar beet, soybean, cotton and canola.

20. A method according to claim 18, in which the locus is a crop which is maize or soybean.

21. A method according to claim 18, in which the locus is a crop selected from maize, sugar beet, soybean, cotton and canola and has been genetically manipulated to confer enhanced tolerance to isoxaflutole or glyphosate.

22. A method according to claim 18, in which the application rate of isoxaflutole is from 20 $gha^{-1}$ to 500 $gha^{-1}$.

23. A method according to claim 18, in which the application rate of isoxaflutole is from 50 $gha^{-1}$ to 150 $gha^{-1}$.

24. A method according to claim 18, in which the application rate of glyphosate is from 250 g to 3000 g acid equivalent (a.e.)ha.

25. A method according to claim 18, in which the application rate of glyphosate is from 400 g to 1000 g acid equivalent (at)/ha.

26. A method according to claim 18, in which the weight ratio of isoxaflutole to glyphosate is from 1:150 to 2:1.

27. A method according to claim 18, in which the weight ratio of isoxaflutole to glyphosate is from 1:20 to 1:2.7.

28. A method for improving the chemical stability of isoxaflutole in a herbicidal composition comprising a herbicidally effective amount of:
   (a) isoxaflutole; and
   (b) glyphosate;
   said method comprising incorporating into we composition:
   (c) a combined amount of (i) polyethylene glycol and (ii) glycerol;
   said composition being in the form of a suspension concentrate;
   said combined amount of (i) and (ii) being an amount effective to improve the chemical stability of isoxaflutole in said suspension concentrate.

29. A herbicidal composition comprising a herbicidally effective amount of:
   (a) isoxaflutole;
   (b) glyphosate; and
   (c) an amount of (i) polyethylene glycol or (ii) glycerol;
   said composition being in the form of a suspension concentrate;
   said amount of (i) or (ii) being an amount effective to enhance the combined herbicidal activity of (a) and (b) in said suspension concentrate.

30. A composition according to claim 29, in which the percentage by weight of polyethylene glycol or glycerol present in the composition is from 15 to 65%.

31. A method for controlling the growth of weeds at a locus which comprises applying to said locus a herbicidal composition comprising a herbicidally effective amount of:
   (a) isoxaflutole;
   (b) glyphosate; and
   (c) an amount of (i) polyethylene glycol or (ii) glycerol;
   said composition being in the form of a suspension concentrate;
   said amount of (i) or (ii) being an amount effective to enhance the combined herbicidal activity of (a) and (b) in said suspension concentrate.

32. A method according to claim 31, in which the locus is a crop selected from maize, sugar beet, soybean, cotton and canola.

33. A method according to claim 31, in which the locus is a crop which is maize or soybean.

34. A method according to claim 31, in which the locus is a crop selected from maize, sugar beet, soybean, cotton and canola and has been genetically manipulated to confer enhanced tolerance to isoxaflutole or glyphosate.

35. A method according to claim 31, in which the application rate of isoxaflutole is from 20 $gha^{-1}$ to 500 $gha^{-1}$.

36. A method according to claim 31, in which the application rate of isoxaflutole is from 50 $gha^{-1}$ to 150 $gha^{-1}$.

37. A method according to claim 31, in which the application rate of glyphosate is from 250 g to 3000 g acid equivalent (a.e.)/ha.

38. A method according to claim 31, in which the application rate of glyphosate is from 400 g to 1000 g acid equivalent (a.e.)/ha.

39. A method according to claim 31, in which the weight ratio of isoxaflutole to glyphosate is from 1:150 to 2:1.

40. A method according to claim 31, in which the weight ratio of isoxaflutole to glyphosate is from 1:20 to 1:2.7.

* * * * *